(12) United States Patent
Chen et al.

(10) Patent No.: US 8,889,841 B2
(45) Date of Patent: Nov. 18, 2014

(54) METHOD FOR PURIFYING REBAUDIOSIDE C

(71) Applicant: International Flavors & Fragrances Inc., New York, NY (US)

(72) Inventors: Zhen Chen, Aberdeen, NJ (US); Ajay Pratap Singh, Highland Park, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 121 days.

(21) Appl. No.: 13/680,290

(22) Filed: Nov. 19, 2012

(65) Prior Publication Data

US 2013/0144046 A1       Jun. 6, 2013

Related U.S. Application Data

(60) Provisional application No. 61/561,483, filed on Nov. 18, 2011.

(51) Int. Cl.
| | | |
|---|---|---|
| *C07H 1/08* | (2006.01) | |
| *C07H 15/24* | (2006.01) | |
| *C07H 15/256* | (2006.01) | |
| *C07H 1/06* | (2006.01) | |

(52) U.S. Cl.
CPC .. *C07H 1/06* (2013.01); *C07H 1/08* (2013.01); *C07H 15/256* (2013.01)
USPC .................................................... 536/5

(58) Field of Classification Search
None
See application file for complete search history.

(56) References Cited

U.S. PATENT DOCUMENTS

| | | | |
|---|---|---|---|
| 4,361,697 A | 11/1982 | Dobberstein et al. ......... 536/128 |
| 4,612,942 A | 9/1986 | Dobberstein et al. ......... 131/276 |
| 2006/0134292 A1 | 6/2006 | Abelyan et al. .............. 426/548 |
| 2007/0082102 A1 | 4/2007 | Magomet et al. ............. 426/548 |
| 2007/0116830 A1 | 5/2007 | Prakash et al. ................ 426/548 |
| 2008/0108710 A1 | 5/2008 | Prakash et al. ................ 514/783 |
| 2008/0226796 A1 | 9/2008 | Lee et al. ...................... 426/590 |
| 2009/0162484 A1 | 6/2009 | Bell et al. ........................ 426/66 |
| 2009/0162487 A1 | 6/2009 | Bell et al. ........................ 426/72 |
| 2010/0267847 A1 | 10/2010 | Yoshinaka et al. ............ 514/777 |
| 2011/0070172 A1 | 3/2011 | Salemme et al. ............... 424/49 |
| 2011/0224311 A1 | 9/2011 | Palmer et al. .................. 514/777 |
| 2012/0157553 A1 | 6/2012 | Dewis et al. ................... 514/777 |
| 2012/0164083 A1 | 6/2012 | Palmer et al. ................... 424/49 |
| 2012/0230922 A1 | 9/2012 | Salemme et al. ............... 424/49 |

FOREIGN PATENT DOCUMENTS

| | | |
|---|---|---|
| CA | 2185496 | 9/1996 |
| CA | 2278083 | 1/2001 |
| CN | 101309598 | 11/2008 |
| CN | 101628924 | 1/2010 |
| JP | 059045848 | 3/1984 |
| WO | WO 2007/142680 | 12/2007 |
| WO | WO 2008/091547 | 7/2008 |
| WO | WO 2011/028671 | 3/2011 |
| WO | WO 2011/037959 | 3/2011 |

OTHER PUBLICATIONS

Schiffman et al. "Investigation of Synergism in Binary Mixtures of Sweeteners" Brain Research Bulletin 1995 38(2):105-120.
Schiffman et al. "Synergism among Ternary Mixtures of Fourteen Sweeteners" Chemical Senses 2000 25:131-140.
Office Communication dated Nov. 6, 2012 from U.S. Appl. No. 12/782,673, filed May 18, 2010.
Office Communication dated Apr. 10, 2013 from U.S. Appl. No. 12/782,673, filed May 18, 2010.
Office Communication dated Jul. 31, 2013 from U.S. Appl. No. 12/782,673, filed May 18, 2010.
Office Communication dated May 3, 2012 from U.S. Appl. No. 12/838,278, filed Jul. 16, 2010.
Office Communication dated Oct. 17, 2012 from U.S. Appl. No. 12/838,278, filed Jul. 16, 2010.
Office Communication dated Jan. 25, 2013 from U.S. Appl. No. 12/838,278, filed Jul. 16, 2010.
Office Communication dated Dec. 28, 2012 from U.S. Appl. No. 13/332,661, filed Dec. 21, 2011.
Notice of Allowance and Fee(s) Due dated May 2, 2013 from U.S. Appl. No. 13/332,661, filed Dec. 21, 2011.
International Preliminary Report on Patentability from PCT/US210/047207, Mar. 15, 2012, PCT.
International Search Report from PCT/US2010/047207, Jan. 25, 2011, PCT.
International Search Report from PCT/US2010/049763, Dec. 14, 2010, PCT.
International Search Report from PCT/US2012/070308, Feb. 26, 2013, PCT.

*Primary Examiner* — Layla Bland
*Assistant Examiner* — Bahar Craigo
(74) *Attorney, Agent, or Firm* — Martin Zhang; XuFan Tseng; Elizabeth M. Quirk

(57) ABSTRACT

The present invention is a method for purifying Rebaudioside C by subjecting "waste material," generated during the Rebaudioside A manufacturing process, to liquid-liquid extraction and recrystallizing the Rebaudioside C.

9 Claims, No Drawings

METHOD FOR PURIFYING REBAUDIOSIDE C

INTRODUCTION

This application claims benefit from U.S. provisional application Ser. No. 61/561,483 filed Nov. 18, 2011, the contents of which are incorporated herein by reference in their entirety.

BACKGROUND OF THE INVENTION

The South American perennial *Stevia rebaudiana* Bertoni is known for its natural sweeteners. The sweetness of the *Stevia* plant is attributed to the presence of high intensity sweet glycosides. The glycosides derived from *Stevia* (steviol glycosides) include stevioside (4-13% dry weight), Rebaudioside A (2-4%), Rebaudioside C (1-2%), dulcoside A (0.4-0.7%) and traces of steviolbioside, rubusoside and Rebaudiosides B, D, E, and F (Kinghorn (2002) Kinghorn (ed.) *Stevia, the Genus Stevia*. Medicinal and Aromatic Plants—Industrial Profiles, Vol. 19. Taylor and Francis, London and NY). Among these glycosides, only stevioside and Rebaudioside A are currently commercially available in large quantities. The raw materials for manufacturing stevioside and Rebaudioside A are the crushed leaves of the perennial shrub. Conventional extraction processes to obtain steviol glycoside-containing extracts that are described in the literature follow similar methodologies: *stevia* leaves are extracted with hot water or alcohols, the extract is clarified by precipitation with salt or alkaline solutions and concentrated, and the extract is re-dissolved in short alcohols (methanol or ethanol) for crystallization of the glycosides.

Methods for extracting Rebaudioside C have also been developed. WO 2011/037959 describes the purification of Rebaudioside C by refluxing a crude *stevia* extract solid or a crude Rebaudioside C solid in a mixed solvent (95% EtOH/MeOH/$H_2O$=12.5/6/2), or (95% propanol/MeOH=12.5/7.5). The solution is subsequently cooled to 22° C. and seeded with 93-98% pure Rebaudioside C crystals. The resulting mixture is left at 22° C. for 16 hours and the white crystalline product is filtered, washed twice with an EtOH/MeOH (4/1) mixture and dried to yield purified Rebaudioside C product. The major drawback of this process is that high purity Rebaudioside C is needed to induce purification. In addition, the yield of this process and the purity of the obtained material are not disclosed.

Chinese Patent No. 102127130 describes a method of purifying Rebaudioside C by passing a crude solution containing about 17% of Rebaudioside C through an ultra-filtration membrane to generate a fraction having a 26% Rebaudioside C content. The fraction is concentrated at 55° C. until the solid content reaches 40%. Subsequently, the liquid and solid are separated such that the solid contains about 33% Rebaudioside C. This crude Rebaudioside C is further purified by recrystallization from a mixed solvent (87% EtOH/68% MeOH/87% acetone=3/2/1) and the resulting purity of Rebaudioside C is 85.4%.

Conventional methods to produce and purify Rebaudioside C require numerous reaction steps or iterative purification steps. There is a need for a simple, efficient, and economical method for production of high purity Rebaudioside C, which can be used in food, beverage, pharmaceutical, cosmetic and other industries.

SUMMARY OF THE INVENTION

This invention features a method for purifying Rebaudioside C. The method of the invention involves the steps of:

(a) extracting a material containing Rebaudioside C and depleted of Rebaudioside A with a solution of ethyl acetate and 1-butanol;
(b) retaining the ethyl acetate and 1-butanol soluble fraction;
(c) contacting the ethyl acetate and 1-butanol soluble fraction with a solution of acetone and water to recrystallize the Rebaudioside C; and
(d) collecting the recrystallized Rebaudioside thereby purifying Rebaudioside C.

In some embodiments, the ratio of ethyl acetate:1-butanol is 60-70:30-40 and the ratio of acetone:water is 80-90:10-20. In other embodiments, the material containing Rebaudioside C and depleted of Rebaudioside A is a solution of tetrahydrofuran and water, wherein the ratio of tetrahydrofuran:water is 20-30:70-80. In further embodiments, the method includes the presteps of extracting the material containing Rebaudioside C and depleted of Rebaudioside A with a first solution of ethyl acetate:1-butanol (80-90:10-20) and discarding the ethyl acetate:1-butanol soluble fraction. In still further embodiments, the method includes the additional step of subjecting the recrystallized Rebaudioside C to a second recrystallization, wherein the second recrystallization employs is a solution of 1-butanol:water (97:3). In yet another embodiment, the recrystallized Rebaudioside C is washed with a solution of acetone:water (85:15).

DETAILED DESCRIPTION OF THE INVENTION

As shown Table 1, HPLC analysis of the "waste material" generated during the Rebaudioside A manufacturing process contains about 17% of Rebaudioside A and 20% of Rebaudioside C along with other glycosides.

TABLE 1

| Retention time (minutes) | Identity | Percent of Total |
| --- | --- | --- |
| 15.974 | Unknown | 16.13 |
| 21.631 | Unknown | 1.95 |
| 22.194 | Unknown | 0.19 |
| 24.425 | Rebaudioside A | 17.18 |
| 24.840 | Stevioside | 20.79 |
| 25.801 | Unknown | 0.27 |
| 26.187 | Rebaudioside F | 2.88 |
| 26.800 | Rebaudioside C | 20.98 |
| 27.444 | Dulcoside A | 2.74 |
| 27.854 | Unknown | 0.27 |
| 28.451 | Stevioside isomer | 2.90 |
| 30.420 | Rubusoside | 1.68 |
| 32.133 | Unknown | 5.90 |
| 33.221 | Steviolbioside | 6.14 |

Given the high percentage of Rebaudioside C in the "waste material" and the utility of Rebaudioside C as a sweetener, the present invention features a method of obtaining high purity Rebaudioside C starting from this "waste material" generated during the Rebaudioside A manufacturing process. According to the instant method, a material containing Rebaudioside C and depleted of Rebaudioside A is extracted with a solution of ethyl acetate/1-butanol and the ethyl acetate/1-butanol soluble fraction is retained. Subsequently, the Rebaudioside C is recrystallized from the ethyl acetate/1-butanol soluble fraction with a solution of acetone/water and the recrystallized Rebaudioside C is collected. Advantageously, the instant method is carried out in the absence of seeding with pure Rebaudioside C crystals.

As used in the context of the present method, "a material containing Rebaudioside C and depleted of Rebaudioside A" is a starting material, in particular a *Stevia* extract or a fraction of a *Stevia* extract, that has had all or a portion of Rebaudioside A removed. In one embodiment, the starting material of the instant method has had 40%, 50%, 60%, 70%, 80%, 90% or 100% of the original amount of Rebaudioside A removed. By way of illustration, whereas *Stevia* leaves have at least twice the amount of Rebaudioside A (2-4%) as Rebaudioside C (1-2%), a material containing Rebaudioside C and depleted of Rebaudioside A may contain equal amounts of Rebaudioside C and Rebaudioside A, or less Rebaudioside A than Rebaudioside C.

In some embodiments, the starting material of the instant method is "a *Stevia*-derived material" containing Rebaudioside C and depleted of Rebaudioside A. In other embodiments, the starting material is a *Stevia* extract or a fraction of a *Stevia* extract prepared by conventional methods.

The starting material can be obtained in solid, semi-solid or liquid form. When in solid or semi-solid form, it is desirable that the starting material is dissolved in an appropriate solvent to facilitate liquid-liquid extraction. In this respect, particular embodiments embrace a starting material that is a solution containing Rebaudioside C and depleted of Rebaudioside A. As demonstrated herein, solid starting material was readily dissolved in a solution of tetrahydrofuran (THF) and water. Accordingly, it is contemplated that solvents with similar polarity as THF, e.g., n-butyl acetate, isobutyl alcohol, methyl isoamyl ketone, or n-propyl alcohol, may also be of use in the instant method as a solvent for dissolving the starting material. However, in particular embodiments, the starting material is dissolved in a solution of tetrahydrofuran (THF) and water. In accordance with this embodiment, the ratio of THF to water is in the range of 20-30 to 70-80 (volume/volume (v/v)). In particular embodiments, the ratio of THF to water 25 to 75 (v/v).

To enrich for Rebaudioside C, the starting material is subjected to a liquid-liquid extraction. In accordance with this step of the instant method, the starting material is extracted one or more times with one or more solutions of ethyl acetate and 1-butanol. In some embodiments, the starting material is extracted one or more times with a solution containing ethyl acetate/1-butanol, wherein the ratio of ethyl acetate to 1-butanol is 60-70 to 30-40 (v/v). In particular, this embodiment embraces a ratio of ethyl acetate to 1-butanol of 75 to 35 (v/v). In other embodiments, low polarity compounds are first removed by extracting the starting material one or more times with a solution containing ethyl acetate/1-butanol, wherein the ratio of ethyl acetate to 1-butanol is 80-90 to 10-20 (v/v). In accordance with the embodiment, the ethyl acetate/1-butanol soluble fraction is discarded and the retentate is further extracted with a second solution of ethyl acetate and 1-butanol.

Accordingly, in one embodiment, extraction of the starting material with a solution of ethyl acetate/1-butanol includes the steps of:

(i) extracting the starting material with a solution containing ethyl acetate and 1-butanol at a ratio of 60-70 to 30-40; and (ii) retaining the ethyl acetate/1-butanol fraction of (i).

In an alternative embodiment, extraction of the starting material with a solution of ethyl acetate/1-butanol includes the steps of:

(i) extracting the starting material with a first solution containing ethyl acetate and 1-butanol at a ratio of 80-90 to 10-20, (ii) discarding the ethyl acetate/1-butanol fraction;

(iii) extracting the retentate of (ii) with a second solution containing ethyl acetate and 1-butanol at a ratio of 60-70 to 30-40; and (iv) retaining the ethyl acetate/1-butanol fraction of (iv).

While it was demonstrated that the starting material was extractable with ethyl acetate/1-butanol solution, other suitable solvents may be used, including for example, 2-butanone, n-propyl alcohol, n-butyl acetate, and isopropanol, used alone or in combination with each other or with ethyl acetate or 1-butanol.

According to the next step of the instant method, the liquid-liquid extraction material or the ethyl acetate and 1-butanol soluble fraction is contacted with a solution of acetone and water to recrystallize the Rebaudioside C. In some embodiments, the ratio of acetone to water is 80-90 to 10-20 (weight/weight (w/w)). In certain embodiments, the ratio of acetone to water is 85 to 15 (w/w). In addition to acetone, it is contemplated that other solvents such as acetonitrile, methanol, ethanol, propanol, isopropanol, butanol, 2-butanol, tert-butanol, or mixtures thereof can be used to recrystallize the Rebaudioside C. To facilitate recrystallization, the mixture can be heated to an elevated temperature of between 40° C. and 60° C., or more preferably between 45° C. and 50° C., and subsequently cooled to approximately room temperature (e.g., 19-22° C.). Upon formation of crystals, the recrystallized Rebaudioside C is collected, e.g., by filtration, and can be dried for storage.

As yet another embodiment, the recrystallized Rebaudioside C can be washed to further enrich the Rebaudioside C. In accordance with this embodiment, the recrystallized Rebaudioside C is washed with a solution of acetone:water at a ratio of 85:15. The mixture can be heated to an elevated temperature of between 40° C. and 60° C., or more preferably between 45° C. and 50° C. for approximately 1 to 3 hours or more preferably 2 hours, and subsequently cooled to approximately room temperature (e.g., 19-22° C.). The mixture is subsequently filtered to collect the solid Rebaudioside C. By including this step, the amount of Rebaudioside C can be enriched to greater than 90%.

As a further embodiment, the instant method can include the additional step of subjecting the recrystallized Rebaudioside C to a second recrystallization, wherein the second recrystallization is a solution of 1-butanol:water (97:3).

Rebaudioside C purified in accordance with the instant method is 70-100% homogeneous with respect to Rebaudioside C and finds use as a sweetener in a variety of food products, dietary supplements, nutraceuticals, pharmaceutical compositions, dental hygienic compositions, tabletop sweeteners and cosmetic products. In addition, the instant Rebaudioside C can be used in the preparation of consumable products, such as food and pharmaceutical products, which retain a desired sweetness but contain lower amounts of a carbohydrate sweetener, such as sugar, and in some cases fewer calories.

The invention is described in greater detail by the following non-limiting examples.

Example 1

Initial Purification of Rebaudioside C from Crude Extracts

Using a variety of different solvent systems, it was observed that a mixture of acetone and water was a suitable solvent for recrystallization of Rebaudioside C from crude starting material (i.e., "waste material" generated during the Rebaudioside A manufacturing process). Accordingly, the yield of recrystallized Rebaudioside C from starting material was determined. For these experiments, crude starting material was mixed with acetone/water (85/15, w/w). Typically, for 1 g of solid, 4-6 g of solvent was used. The mixture was heated to 48° C. and all of the solid was allowed to dissolve. The mixture was cooled to room temperature and stirred for 3-4 days. The solution was filtered to collect the white precipitate, which was then washed with acetone and dried under vacuum at 50° C. for 8 hours.

TABLE 2

| Amount of Crude Starting Material | Reb C content in crude | Amount of Solid obtained | Reb C Content in Solid | Reb C Recovery Yield |
|---|---|---|---|---|
| 5 g | 24.5% | 0.9 g | 77.0% | 56.6% |
| 5 g | 32.5% | 1.4 g | 69.6% | 60.0% |
| 5 g | 32.5% | 1.3 g | 76% | 60.8% |
| 20 g | 32.5% | 5.2 g | 75.6% | 60.5% |
| 6.0 g | 36.4% | 1.84 g | 76.8% | 64.7% |
| 6.84 g | 40.7% | 2.37 g | 74.3% | 63.2% |
| 16 g | 44.0% | 6.34 g | 80.0% | 72.0% |
| 14 g | 44.0% | 6.08 g | 81.7% | 80.6% |

Reb C, Rebaudioside C.

This analysis indicated that the "waste material" was not optimal for direct recrystallization of Rebaudioside C and that starting material containing a higher content of Rebaudioside C, yielded a solid with higher purity and yield. Accordingly, to increase purity and yield, the starting material was subjected to liquid-liquid extraction with different solvents.

Twenty grams of Rebaudioside C starting material was dissolved in 500 ml of acetone, which contained 70-80 of water (v/v). The solution was extracted two times with 500 ml of ethyl acetate which contained 15% of 1-butanol (v/v). The 1-butanol/ethyl acetate layer mainly contained less polar compounds and was therefore discarded. Subsequently, the acetone/water phase was further extracted two times with 500 ml of ethyl acetate that contained 30-40% 1-butanol (v/v). The ethyl acetate/1-butanol layers were combined and concentrated under vacuum to provide enriched Rebaudioside C material. The resulting yield and content of liquid-liquid extraction with acetone/water and ethyl acetate/1-butanol are presented in Table 3.

TABLE 3

| Solvent for Dissolving the Starting Material (ratio, v/v) | Extraction solvent (ratio, v/v) | Reb C Content | Reb C Recovery Yield |
|---|---|---|---|
| Acetone/water (20/80) | Ethyl acetate/1-butanol (65/35) | 30.24% | 79.38% |
| Acetone/water (30/70) | Ethyl acetate/1-butanol (65/35) | 31.95% | 62.30% |

In another series of experiments, twenty grams of the starting material was dissolved in 500 ml of THF, which contained 65-80 of water (v/v). The solution was extracted two times with 500 ml of ethyl acetate which contained 15% of 1-butanol (v/v). The ethyl acetate/1-butanol layer mainly contained less polar compounds and was therefore discarded. Subsequently, the THF/water phase was further extracted two times with 500 ml of ethyl acetate which contained 30-40% of 1-butanol (v/v). The 1-butanol/acetate layers were combined and concentrated under vacuum to provide enriched Rebaudioside C material. The resulting yield and content of liquid-liquid extraction with THF/water and ethyl acetate/1-butanol are presented in Table 4.

TABLE 4

| Solvent for Dissolving the Starting Material (ratio, v/v) | Extraction solvent (ratio, v/v) | Reb C Content | Reb C Recovery Yield |
|---|---|---|---|
| THF/water (20/80) | Ethyl acetate/1-butanol (65/35) | 28.5% | 61.98% |
| THF/water (35/65) | Ethyl acetate/1-butanol (65/35) | 29.27% | 49.02% |
| THF/water (30/70) | Ethyl acetate/1-butanol (70/30) | 31.35% | 70.53% |
| THF/water (25/75) | Ethyl acetate/1-butanol (65/35) | 28.02% | 60.0% |

This analysis indicated that the highest Rebaudioside C content and recover was obtained when using THF/water as the solvent for the starting material, wherein the ratio of THF:water was in the range of 20-30:70-80. In addition, this analysis indicated that a suitable ethyl acetate:1-butanol ratio was in the range of 60-70:30-40.

Example 2

Purification of Rebaudioside C

Twenty grams of the starting material was dissolved in 500 ml of THF/water mixture, which contained 70-80% of water, preferably 75% (v/v). The resulting solution was extracted two times with 500 ml of ethyl acetate/1-butanol mixture (85/15, v/v). The 1-butanol/ethyl acetate layer was removed.

Subsequently, the THF-water phase was further extracted two times with 500 ml of ethyl acetate/butanol mixture, which contained 30-40% of 1-butanol, preferably 35% (v/v). The ethyl acetate/butanol layers of these two extractions were combined and concentrated under vacuum to provide 8.70 g of material. The Rebaudioside C content of this material reached 24.5% (Table 5), as determined by HPLC analysis.

TABLE 5

| Retention time (minutes) | Identity | Percent of Total |
|---|---|---|
| 12.702 | Unknown | 1.10 |
| 15.722 | Unknown | 4.62 |
| 18.547 | Unknown | 4.20 |
| 22.811 | Unknown | 1.06 |
| 24.473 | Rebaudioside A | 16.73 |
| 24.931 | Stevioside | 25.26 |
| 25.780 | Unknown | 0.15 |
| 26.197 | Rebaudioside F | 2.81 |
| 26.968 | Rebaudioside C | 24.50 |
| 27.562 | Dulcoside A | 3.44 |
| 27.951 | Unknown | 0.22 |
| 28.579 | Stevioside isomer | 3.71 |
| 30.543 | Rubusoside | 9.20 |
| 32.216 | Unknown | 2.72 |
| 33.485 | Steviolbioside | 0.26 |

Using an acetone/water mixture, which contained 10% to 20% of water (by weight), preferably 15%, it was observed that the liquid-liquid extraction material was suitable for recrystallization. Five grams of liquid-liquid extraction material (Rebaudioside C content of 24.5%) was mixed with 27.5 g of acetone/water (15/85, w/w), and the mixture was heated mixture to 48° C. The clear solution obtained was cooled to room temperature (i.e., 19-22° C.) and stirred for 4 days. The solution was filtered to collect the white precipitate, which was subsequently washed with acetone and dried under vacuum at 50° C. for 8 hours. The recrystallized material (0.9 g) was observed to have a Rebaudioside C content of 76.98% (Table 6), as determined by HPLC analysis. Moreover, the recovery yield of Rebaudioside C was 56.6%.

TABLE 6

| Retention time (minute) | Identity | Percent of Total |
|---|---|---|
| 18.712 | Unknown | 2.34 |
| 24.363 | Rebaudioside A | 6.82 |
| 24.781 | Stevioside | 6.59 |
| 26.193 | Rebaudioside F | 0.85 |
| 27.015 | Rebaudioside C | 76.98 |
| 27.557 | Dulcoside | 0.75 |
| 27.995 | Unknown | 0.39 |
| 28.578 | Stevioside isomer | 0.92 |
| 30.566 | Rubusoside | 0.76 |
| 31.325 | Rebaudioside B | 2.08 |

The purity of Rebaudioside C could be further increased by a second recrystallization. The second recrystallization involved mixing 2 grams of the material resulting from the first recrystallization with 27.5 g of 1-butanol/water (97/3, w/w), and heating the mixture to 78° C. The clear solution obtained was cooled to room temperature (i.e., 19-22° C.) and allowed to stand for 2 days. The solution was filtered to collect the white precipitate, which was subsequently washed with acetone and dried under vacuum at 50° C. for 8 hours. The second recrystallization yielded 1.1 grams of material with a Rebaudioside C content of 93.0% (Table 7), as determined by HPLC. Moreover, the recovery yield was 78.7%.

TABLE 7

| Retention time (minutes) | Identity | Percent of Total |
|---|---|---|
| 24.082 | Rebaudioside A | 5.30% |
| 26.530 | Rebaudioside C | 93.0% |
| 27.599 | Dulcoside A | 0.37% |
| 32.201 | Unknown | 1.38% |

Also, the purity of Rebaudioside C could be further increased by including a washing step. The washing step involved mixing 5 grams of the material resulting from the first recrystallization with 100 grams of acetone/water (85/15, w/w), and heating the mixture to 58° C. The mixture was refluxed for 2 hours and was cooled to room temperature (i.e., 19-22° C.) and allowed to stand for 16 hours. The solution was filtered to collect the white solid, which was subsequently washed with acetone and dried under vacuum oven at 50° C. for 8 hours. The washing step yielded 3.6 grams of material with a Rebaudioside C content of 91.1% (Table 8), as determined by HPLC. Moreover, the recovery yield was 84.3%.

TABLE 8

| Retention time (minute) | Identity | Percent of Total |
|---|---|---|
| 25.362 | Rebaudioside A | 3.63 |
| 25.641 | Stevioside | 0.68 |
| 26.264 | Rebaudioside F | 0.83 |
| 26.658 | Rebaudioside C | 91.12 |
| 27.048 | Dulcoside | 1.75 |
| 27.419 | Stevioside isomer | 0.65 |
| 29.825 | Unknown | 1.35 |

What is claimed is:

1. A method for purifying Rebaudioside C comprising
   (a) extracting a material containing Rebaudioside C and depleted of Rebaudioside A with a solution of ethyl acetate and 1-butanol;
   (b) retaining the ethyl acetate and 1-butanol soluble fraction;
   (c) contacting the ethyl acetate and 1-butanol soluble fraction with a solution of acetone and water to recrystallize the Rebaudioside C; and
   (d) collecting the recrystallized Rebaudioside C thereby purifying Rebaudioside C.

2. The method of claim 1, wherein the ratio of ethyl acetate:1-butanol is 60-70:30-40.

3. The method of claim 1, wherein the ratio of acetone:water is 80-90:10-20.

4. The method of claim 1, wherein the material containing Rebaudioside C and depleted of Rebaudioside A comprises tetrahydrofuran and water.

5. The method of claim 4, wherein the ratio of tetrahydrofuran:water is 20-30:70-80.

6. The method of claim 1, further comprising the presteps of extracting the material containing Rebaudioside C and depleted of Rebaudioside A with a first solution of ethyl acetate:1-butanol (80-90:10-20) and discarding the ethyl acetate:1-butanol soluble fraction.

7. The method of claim 1, further comprising subjecting the recrystallized Rebaudioside C to a second recrystallization.

8. The method of claim 7, wherein the second recrystallization comprises a solution of 1-butanol:water (97:3).

9. The method of claim 1, further comprising washing the recrystallized Rebaudioside C with a solution of acetone:water (85:15).

* * * * *